United States Patent
Wicherski et al.

[11] Patent Number: 5,868,768
[45] Date of Patent: Feb. 9, 1999

[54] METHOD AND DEVICE FOR ENDOLUMINAL DISRUPTION OF VENOUS VALVES

[75] Inventors: Jan Wicherski, San Diego; Stephen A. Sosnowski, Oceanside, both of Calif.

[73] Assignee: Baxter International Inc., Deerfield, Ill.

[21] Appl. No.: 833,155

[22] Filed: Apr. 4, 1997

Related U.S. Application Data

[63] Continuation of Ser. No. 485,616, Jun. 7, 1995, Pat. No. 5,658,302.

[51] Int. Cl.$^6$ .................................................. A61B 17/00
[52] U.S. Cl. .......................... 606/159; 606/170; 604/22
[58] Field of Search ................................ 606/1, 159, 167, 606/170, 171; 604/22

[56] References Cited

U.S. PATENT DOCUMENTS

| | | |
|---|---|---|
| 2,676,595 | 4/1954 | Dyekjaer et al. . |
| 3,837,345 | 9/1974 | Matar . |
| 4,493,321 | 1/1985 | Leather . |
| 4,528,982 | 7/1985 | Wellenstam . |
| 4,576,162 | 3/1986 | McCorkle . |
| 4,655,217 | 4/1987 | Reed . |
| 4,729,374 | 3/1988 | Alfranca . |
| 4,733,669 | 3/1988 | Segal . |
| 4,765,332 | 8/1988 | Fischell et al. . |
| 4,768,508 | 9/1988 | Chin et al. . |
| 4,898,575 | 2/1990 | Fischell et al. . |
| 4,952,215 | 8/1990 | Ouriel et al. . |
| 4,994,067 | 2/1991 | Summers . |
| 5,026,383 | 6/1991 | Nobles . |
| 5,069,679 | 12/1991 | Taheri . |
| 5,087,264 | 2/1992 | Miller et al. . |
| 5,087,265 | 2/1992 | Summers . |
| 5,100,424 | 3/1992 | Jang et al. . |
| 5,141,491 | 8/1992 | Bowald . |
| 5,152,771 | 10/1992 | Sabbaghian et al. . |
| 5,171,316 | 12/1992 | Mehigan . |
| 5,192,268 | 3/1993 | Shiber . |
| 5,224,949 | 7/1993 | Gomringer et al. . |
| 5,234,450 | 8/1993 | Segalowitz . |
| 5,242,461 | 9/1993 | Kortenbach et al. . |
| 5,282,813 | 2/1994 | Redha . |
| 5,284,478 | 2/1994 | Nobles et al. . |
| 5,522,824 | 6/1996 | Ashby ..................................... 606/159 |
| 5,554,163 | 9/1996 | Schturman ............................. 606/159 |

FOREIGN PATENT DOCUMENTS

| | | |
|---|---|---|
| 3942-589 | 7/1991 | Germany . |
| WO 89/06936 | 8/1989 | WIPO . |

OTHER PUBLICATIONS

N. L. Mills & J. L. Ochsner, "Valvulotomy of valves in the sphenous vein graft before coronary artery bypass." Biosurgery, vol. 71, No. 6, pp. 878–879, Jun. 1976–Feb. 23, 1988.

"The New Hall Valvulotome," product leaflet published by Solco Basle, Inc., 1990.

"Insitucat Valvulotome," product leaflet published by Aesculap, date unknown.

"Leather Retrograde Valvulotome," product leaflet published by Baxter International., Inc., 1990.

"The Olympus Valvulotomes," product leaflet published by Olympus Corporation, 1990.

"The LeMaitre Valvulotome System," product leaflet published by Vascutech, Inc., date unknown.

"Leather Karmody in Situ Bypass Set," product leaflet published by American Hospital Suppply Corp., 1984.

Baxter Healthcare Corp. Catalog, pp. E115–E116, shoeing three types of Leather brand valvulotome, 1988.

Pilling catalog, p. 226, showing Mills Valvulotome, Obarctation hook, and other, unumbered pages showing DeBakey valve hooks, and other microsurgery instruments, date unknown.

*Primary Examiner*—William Lewis
*Attorney, Agent, or Firm*—Robert Buyan; Raymond Sun; Guy Cumberbatch

[57] ABSTRACT

A method and device for cutting venous valve located within the lumen of a vein. The device comprises an elongate shaft of rigid or flexible construction and a valvulotome blade positioned on the distal end of said elongate shaft. The valvulotome blade comprises an elongate shank portion which is disposed substantially parallel to the longitudinal axis of the shaft, and a head portion which extends laterally from the shank portion of the blade. The head portion of the blade comprises an outer venous wall abutment surface and a proximal cutting surface. The venous wall abutting surface is a spaced distance from the proximal cutting surface such that the venous wall abutment surface may be forced into abutment with the venous wall and the device may be drawn through a venous valve such that the proximal cutting surface will cut the venous valve, but will not come into contact with the adjacent vein wall. The device may incorporate a mechanism, such as a protruding loop of wire, which will abut against the blood vessel wall so as to force the venous wall abutment surface of the valvulotome blade against the opposite wall of the vein or during the venous valve cutting procedure. The method of the invention provides for operation of the device to effect cutting of venous valve, and may be performed concurrently with an in situ side branch occlusion procedure. The method is preferably performed under angioscopic guidance, and the angioscope used for guidance of the method may be integrated with a separate side branch occlusion device to facilitate concurrent performance of the side branch occlusion procedure and the venous valve cutting procedure.

37 Claims, 5 Drawing Sheets

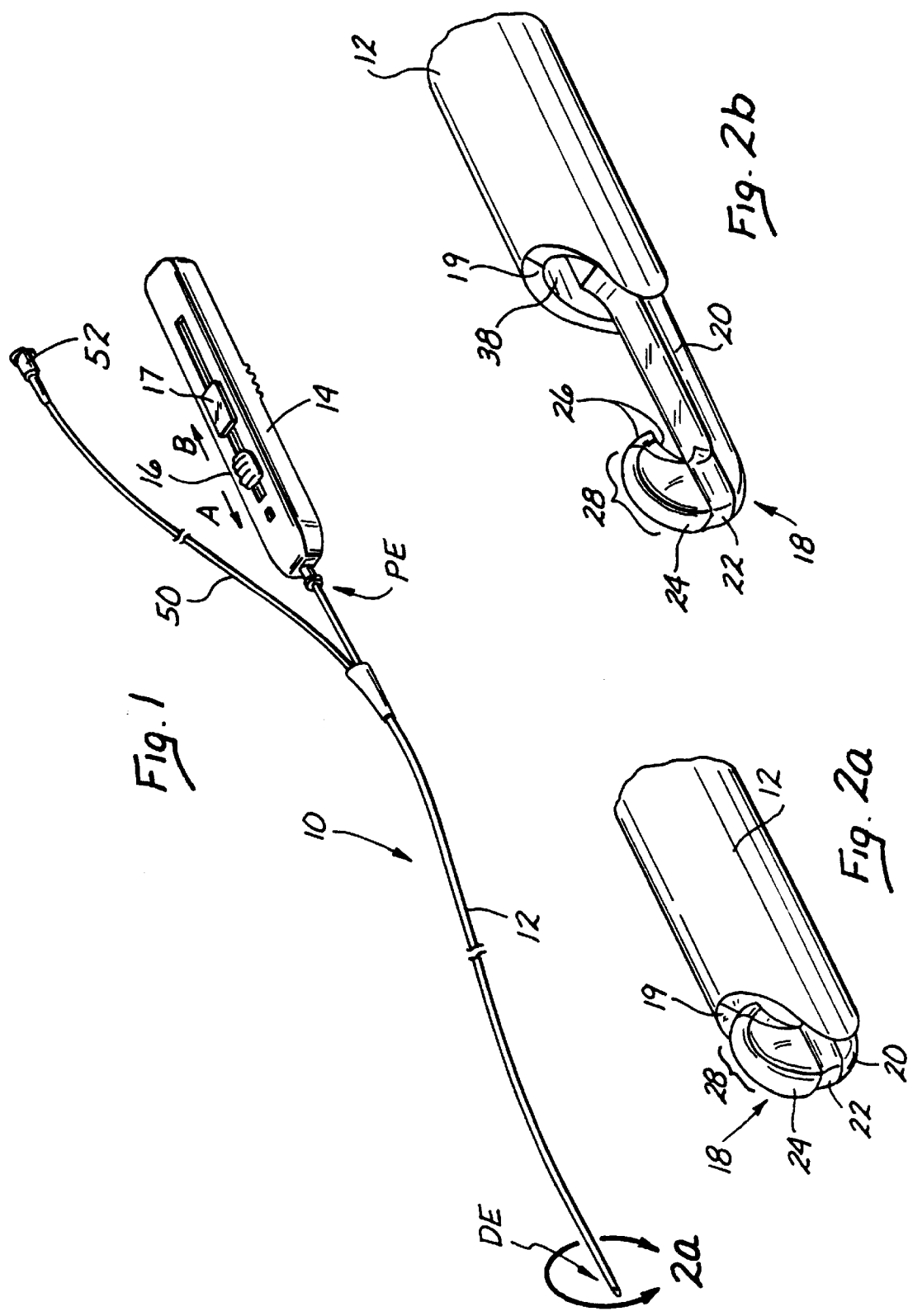

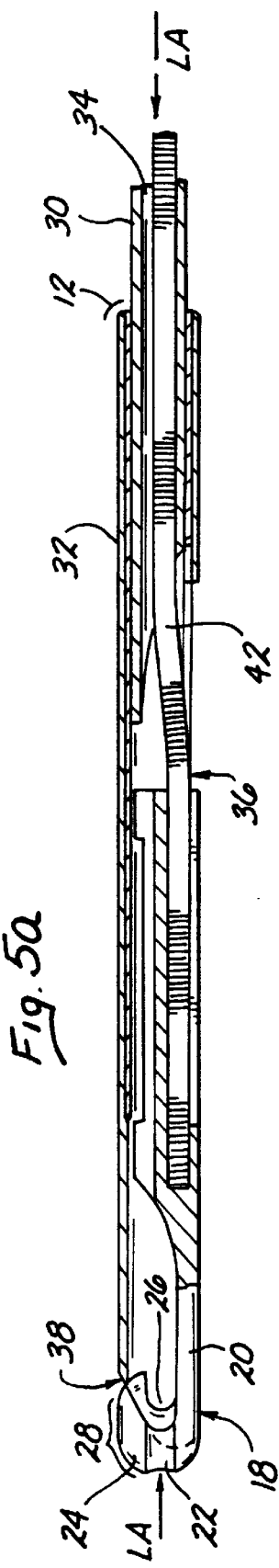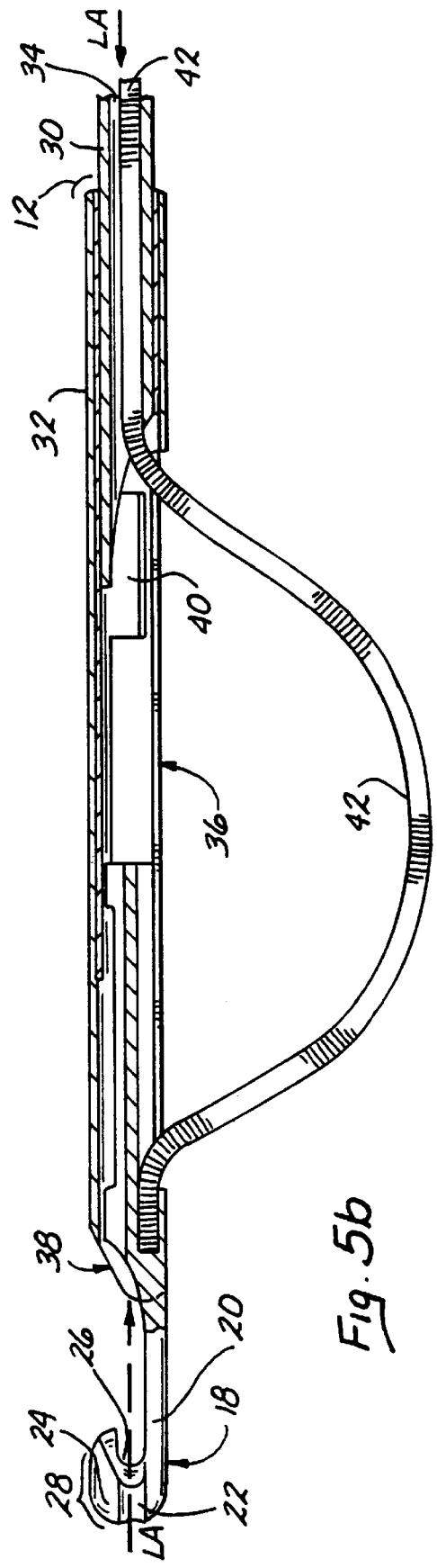

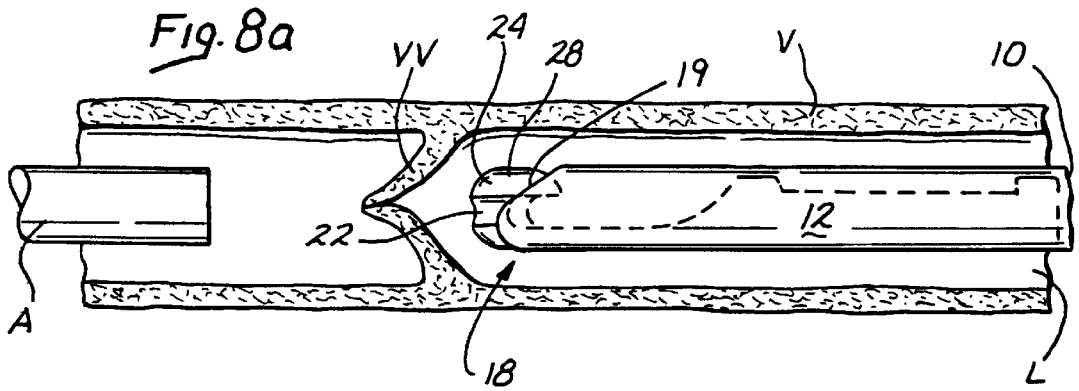
Fig. 8a
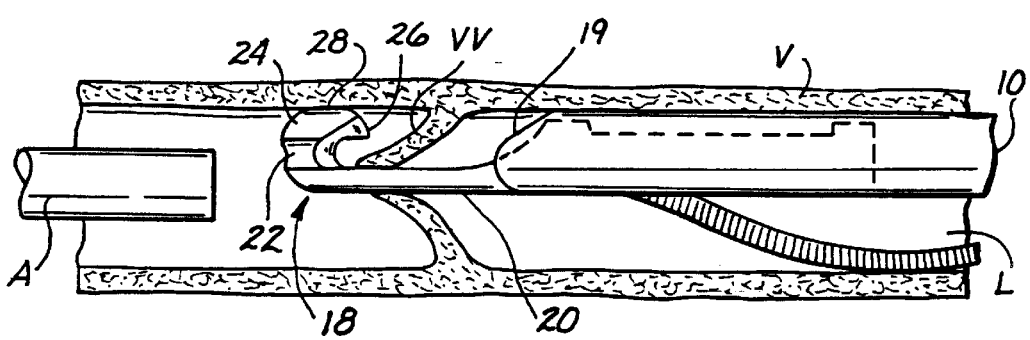
Fig. 8b
Fig. 8c

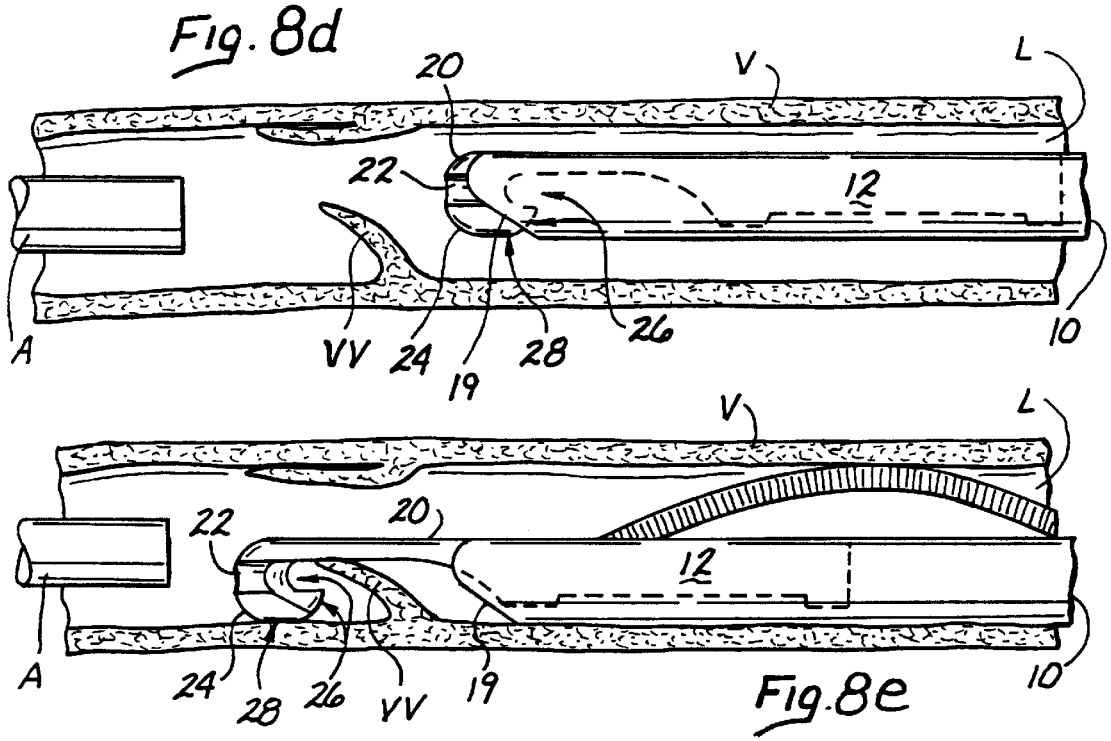
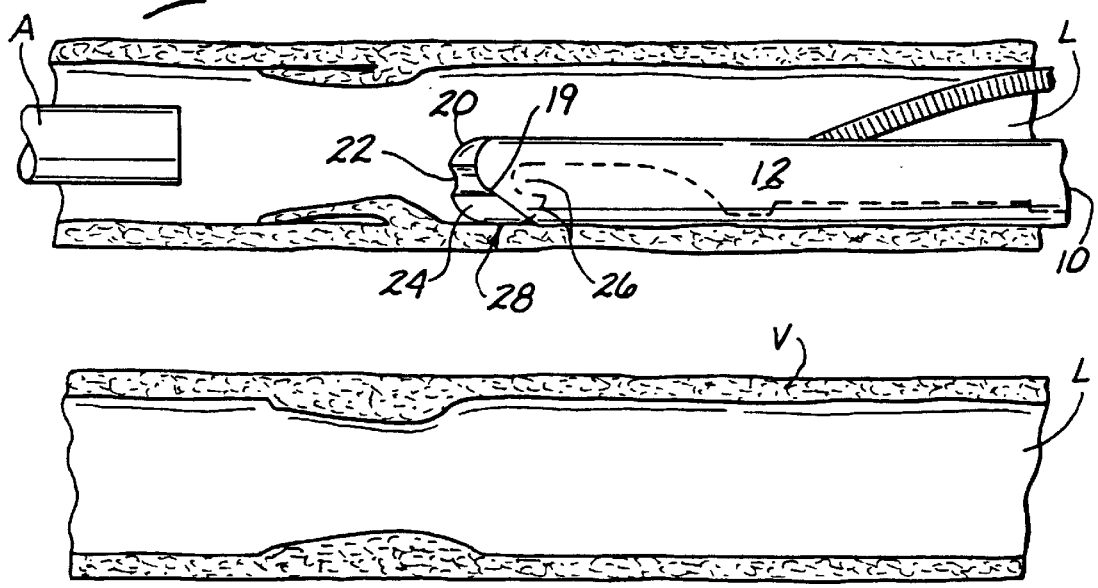

METHOD AND DEVICE FOR ENDOLUMINAL DISRUPTION OF VENOUS VALVES

RELATED APPLICATION

This is a continuation of U.S. patent application Ser. No. 08/485,616, filed Jun. 7, 1995, now U.S. Pat. No. 5,658,302.

FIELD OF THE INVENTION

The present invention relates generally to medical methods and devices, and more particularly to a method and device for cutting or disrupting venous valves located in a mammalian vein.

BACKGROUND OF THE INVENTION

Many mammalian veins are known to have semilunar venous valves located within their lumens for preventing back flow of blood therethrough. In human beings, venous valves are most numerous in the large veins (i.e., those greater than 1/12 in. in diameter) of the extremities, especially of the lower extremities.

In a number of reconstructive vascular surgical procedures, segments of vein are utilized as grafts for replacing or bypassing occluded segments of artery.

For example, in coronary artery bypass graft (CABG) procedures, a segment of saphenous vein may be removed from the patient's leg, prepared for use as a graft, and anastimosted to an occluded coronary artery so as to form a bypass conduit around the coronary artery occlusion. In these saphenous vein CABG procedures, it is typical for the surgeon to prepare the harvested segment of vein for use as a graft by a) inserting an instrument known as a "valvulotome" into the lumen of the vein segment and using such instrument to disrupt the venous valves located therein and also b) reversing the directional orientation of the harvested segment of vein (i.e., turn it end for end) prior to implantation. The disruption of the venous valves and reversal of the directional orientation of the vein segment avoids any potential for any venous valves to remain competent within the harvested graft segment or to interfere with subsequent blood flow through the graft.

Similarly, in in situ vein bypass procedures, a segment of saphenous vein is utilized to bypass one or more blockages in the artery(s) of the leg. In such in situ bypass procedures, the saphenous vein is initially exposed and transected at sites above and below the arterial blockage. Thereafter, a valvulotome device is passed through the lumen of the transected segment of vein and utilized to disrupt all venous valves located therewithin. Thereafter, all side branches or tributaries of the vein segment are ligated or blocked, thereby rendering the vein segment usable as a bypass conduit for the arterial circulation. After the vein segment has been prepared in this manner, the transected ends of the vein segment are anastomosed to the occluded artery, at sites above and below the blockage. In this regard, the prepared vein segment forms an in situ bypass conduit around the arterial blockage.

In both CABG and in situ vein bypass procedures, it is important to make certain that all venous valves located within the vein segment to be utilized as the bypass graft, have been lysed or otherwise rendered incompetent. Numerous venous valve cutting devices or "valvulotomes" have heretofore been utilized for this purpose.

Examples of previously known valvulotome devices, vein stripping apparatus, and other related devices/methods are described in U.S. Pat. Nos. 5,284,478 (Nobles et al), 5,282,813 (Redha), 5,234,450 (Segalowitz), 5,224,949 (Gomringer et al.), 5,192,268 (Shiber), 5,141,491 (Bowald), 5,092,872 (Segalowitz), 5,087,264 (Miller et al.), 5,133,725 (Quadri), 5,152,771 (Sabbaghian et al.), 5,092,872 (Segalowitz), 5,087,265 (Summers), 5,049,154 (Quadri), 5,026,383 (Nobles), 4,952,215 (Ouriel et al.), 4,898,575 (Fischell et al.), 4,768,508 (Chin et al.), 4,729,374 (Alfranca), 4,544,217 (Reed), 4,493,321 (Leather), 3,837,345 (Matar), 2,676,595 (Dyekjaer), 5,171,316 (Mehigan), and in foreign patents/patent publications Nos. FR 2649-309-A (Formichi), 2,044,103A (Ross et al.), FR 002679437 A (Valici), DE 4020-155-A (Storz), PCT WO 93/20764 (Goldberg et al.), WO 92/08414 (Berkshire Inc.), WO 91/01689 (Segalowitz), WO 90/02523 (Bestimmungsstaaten), WO 89/09029 (Taheri), WO 89/06936 (Bowald), WO 88/00458 (Fischell), and 0 248 761 A1 (Fogarty).

In any valvulotome device, it is desirable for the cutting surface(s) of the device to be configured and designed to effectively cut the cusps of the venous valve at sufficient depth to render the valve fully incompetent without causing damage or trauma to the wall intimal surface of the vein. Failure to cut the valve cusps deeply enough may allow remnants of the valve cusps to continue to obstruct flow through the lumen of the vein segment. On the other hand, passage of the cutting surface(s) of the device into the luminal wall of the vein may result in frank perforation of the vein, or may otherwise render the vein segment unusable for use as a graft.

In view of the above-explained considerations, there remains a need in the art for the development of improved valvulotome devices which are capable of causing reproducible and consistent lysis of venous valves, while minimizing any potential for traumatization of the wall or intimal layer of the vein in which they are deployed.

SUMMARY OF THE INVENTION

The device of the present invention comprises a valvulotome which is usable to disrupt venous valves with the lumen of the vein. The valvulotome device of the present invention comprises: an elongate shaft or catheter body having a control wire member extending longitudinally therethrough. A valvulotome blade is positioned on the distal end of the shaft or catheter body, and is connected to the distal end of the control wire, such that back and forth movement of the control wire will cause back and forth movement of the valvulotome blade, relative to the shaft or catheter body. The valvulotome blade has a configuration comprising and elongate shank portion, which is disposed substantially parallel longitudinal axis of the shaft or catheter body, and a head portion which extends laterally from the shank portion of the blade. The head portion of the blade has a proximal cutting edge, and a lateral venous wall abutting surface. The venous wall abutting surface is of smooth configuration so as to ride in abutment with the luminal wall of the vein without causing trauma thereto. The proximal cutting edge of the valvulotome blade is formed at a spaced distance from the venous wall abutment surface so as to cut the cusps of the venous valves deeply enough to result in complete incompetence of the valve cusp, while avoiding cutting of the luminal wall of the vein.

In accordance with the present invention, the control wire and valvulotome blade are longitudinally movable back and forth, relative to the shaft or catheter body, such that the valvulotome blade may alternately be positioned in: i) a distally retracted position wherein the proximal cutting surface of the valvulotome blade is surrounded and shielded by the distal end of the shaft or catheter body; and ii) a distally extended position wherein the proximal cutting surface of the valvulotome blade is located a spaced distance ahead of the distal end of the shaft or catheter body, so as to be usable for cutting of a venous valve.

Further in accordance with the invention, the distal end of the shaft or catheter body may be specifically configured such that, when the valvulotome blade is in its proximally retracted position, the cutting surface of the valvulotome will nest or seat within the distal end of the shaft or catheter body, thereby fully shielding the cutting surface of the valvulotome blade and preventing inadvertent trauma to the surrounding tissues, and also forming a smooth distal tip on the device, to facilitate advancement of the device through the vasculature.

Further in accordance with the invention, one or more fluid infusion lumens may extend longitudinally through the device, for infusion of fluid (e.g. saline solution or Ringer's lactate solution) during use of the valvulotome device.

Further in accordance with the invention, a lateral slot opening may be formed near the distal end of the device lumen such that a segment of the control wire may bulge or protrude laterally in a first direction, away from the shaft or catheter body. Such bulging or protrusion of the guidewire in the first direction causes the shaft or catheter body and valvulotome cutting blade to be propelled or forced in the opposite direction, thereby facilitating positioning of the valvulotome blade in the desired abutting contact with the contralateral surface of the lumen of the vein in which the device is positioned.

In accordance with the method of the present invention, a valvulotome device of the foregoing character may be inserted into the vasculature by open surgical cutdown, or by percutaneous insertion methodology. At the time of insertion, the valvulotome cutting blade is in its distally retracted position such that the cutting surface of the blade is fully shielded by the distal end of the shaft or catheter body. Thereafter, the device is advanced through vasculature to a position whereat the distal end of the device is positioned immediately upstream of a venous valve. Thereafter, the control wire and the valvulotome cutting blade are advanced in the distal direction, such that the cutting blade advances through the venous valve, and the control wire protrudes laterally out of the shaft or catheter body, in the first direction. This causes the shaft or catheter body and valvulotome cutting blade to move into abutment with the contralateral luminal surface of the vein, such that the venous wall abutment surface of the valvulotome cutting blade is in abutment with the venous wall, and such that the cutting surface of the valvulotome cutting blade is positioned to effect the desired cutting of a cusp of the venous valve. Thereafter, the device is drawn in the proximal direction such that the cutting surface of the valvulotome cutting blade effects the desired cutting of the venous valve. Thereafter, the control wire and valvulotome cutting blade are retracted to the proximally retracted position, the device is rotated 180°, and the above-described procedure is repeated to effect cutting of the opposite cusp of the venous valve. This results in complete lyses, and effective incompetency of the venous valve. The usage of the device of the present invention, in the above-described manner, may be visualized and observed through the use of an angioscope or by any other suitable means.

Various other objects and advantages of the invention will become apparent to those skilled in the art upon reading and understanding of the following detailed description, and consideration of the accompanying drawings.

BRIEF DESCRIPTION OF THE DRAWINGS

FIG. 1 is a perspective view of a preferred valvulotome device of the present invention.

FIG. 2a is an enlarged perspective view of the device shown in FIG. 1, with the valvulotome blade in its retracted position.

FIG. 2b is an enlarged perspective view of the distal end of the device shown in FIG. 1 with the valvulotome blade in its extended position.

FIG. 5a is a longitudinal sectional view of the distal portion of the device of FIG. 1, with the valvulotome blade in its retracted position.

FIG. 5b is a longitudinal sectional view of the distal portion of the device of FIG. 1 with the valvulotome blade and positioning wire in their extended positions.

FIGS. 8a–8g are a step-by-step illustration of a preferred method of disrupting venous valves by use of the device shown in FIGS. 1–7.

DETAILED DESCRIPTION OF THE PREFERRED EMBODIMENT

Figure 4:
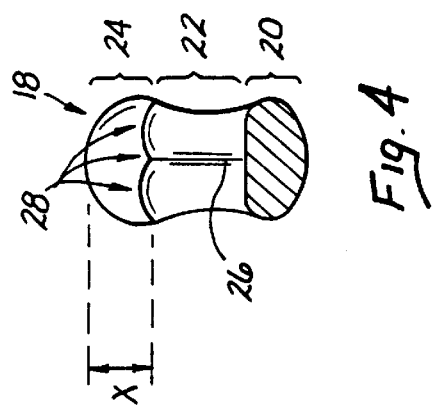
FIG. 4 is a cross-sectional view through line 4—4 of FIG. 3.
Figure 3:
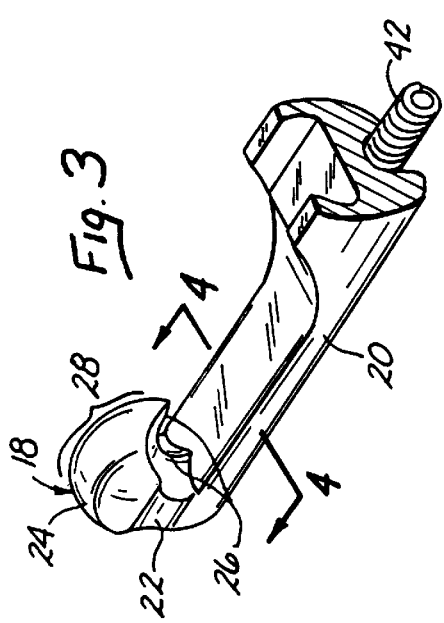
FIG. 3 is a rear perspective view of the valvulotome blade portion of the valvulotome device shown in FIG. 1.
Figure 6:
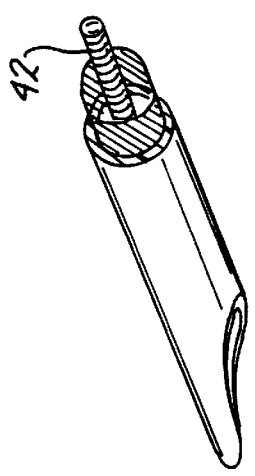
FIG. 6 is a rear perspective view of an insert member which forms a portion of the device shown in FIGS. 5a & 5b.
Figure 7:
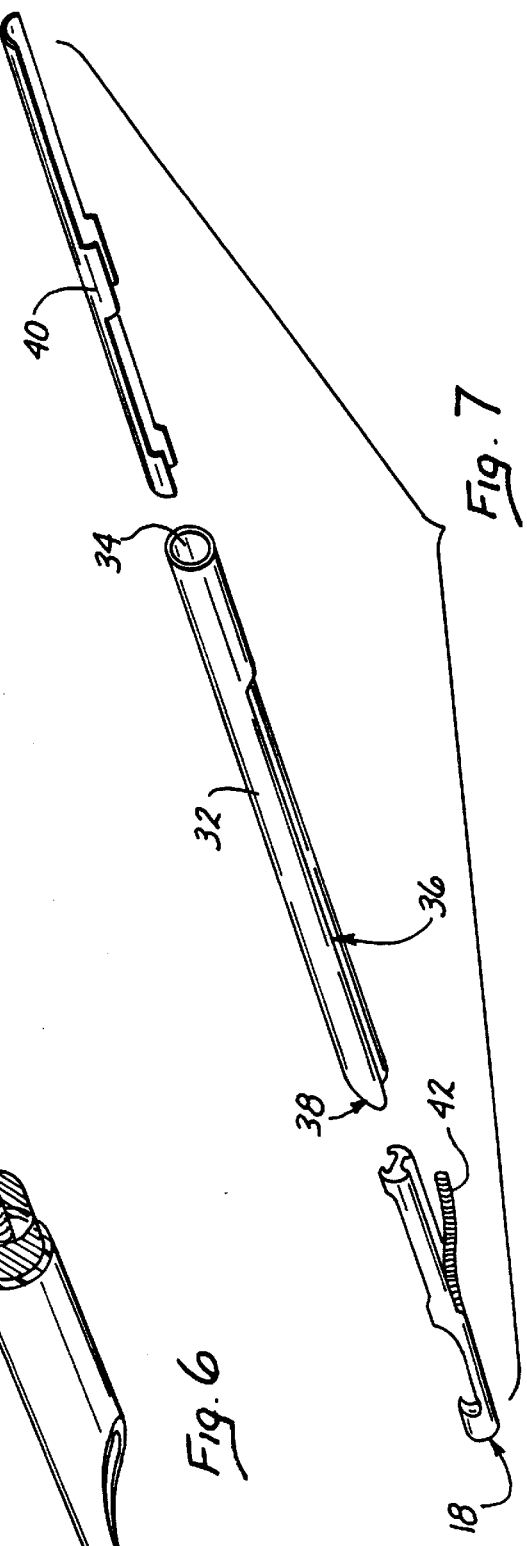
FIG. 7 is an exploded perspective view of the valvulotome blade and distal insert assembly which forms a portion of the device shown in FIGS. 5a & 5b.

The following detailed description and the accompanying drawings are provided for purposes of describing and illustrating presently preferred embodiments of the invention only, and are not intended to limit the scope of the invention in any way.

A. The Preferred Device

With reference to the drawings, the preferred valvulotome device 10 of the present invention comprises an elongate shaft or catheter body 12 having a proximal end PE, a distal end DE and a longitudinal axis LA extending longitudinally therethrough. Depending on the type of procedure in which the device 10 is to be used, the elongate shaft or catheter body 12 may be of either rigid or pliable construction. Notably, when the device 10 is intended for percutaneous insertion and advancement through tortuous vasculature, the elongate shaft or catheter body 12 will typically comprise a pliable or flexible tube of a type commonly employed in the construction of cardiovascular catheters. On the other hand, in applications wherein the valvulotome device 10 is to be inserted into a previously harvested segment of vein, the elongate shaft or catheter body 12 may be of rigid construction, as the intended procedure would require no bending or flexing of the shaft or catheter body 12 during use. In the embodiment described herein, the elongate shaft or catheter body 12 is referred to in terms of a pliable "catheter body", but it will be appreciated that such term shall also apply to various rigid or semi-rigid cannulae or tubular shafts.

A handpiece 14 is positioned on the proximal end PE of the catheter body 12 and includes a sliding actuator 16 which, when moved back and forth, will cause concurrently back and forth movement of a valvulotome blade 18 located on the distal end DE of the catheter body 12. In this regard, the actuator 16 may be utilized to move the valvulotome blade 18 back and forth between its retracted position (FIGS. 2a, 5a) and its extended position (FIGS. 2b, 5b).

As is clearly shown in FIGS. 2–5, the preferred valvulotome blade 18 comprises a rigid member having an elongate shank portion 20 which extends parallel to the longitudinal axis LA of the catheter body 12. A lateral head portion 24 extends laterally from the distal end of the elongate shank portion 20, and incorporates a narrowed frenulum 22. A smooth venous wall abutment surface 28 is formed on the outer lateral surface of the head member 24. The cutting edge 26 is formed on the proximal surface of the head member 24. The cutting edge 26 is preferably of concaved configuration, and extends from the inner edge of the shank portion 20, to a location which is as spaced distance X (FIG. 4), which is preferably 0.020–0.025 inch, from the outermost extent of the lateral venous wall abutment surface 28, as shown in FIG. 4. Such preferred space X between the cutting edge 26 and the venous wall abutment surface 28 ensures that the valvulotome cutting blade 18 may be used to effectively cut the venous valve without establishing contact between the cutting surface 26 of the blade 18 and the luminal wall of the vein.

Also, in the preferred embodiment, the distal end of the catheter body 12 has a generally s-shaped or curved beveled distal surface 19 which is configured to correspond to the shape of the cutting edge 26 of the valvulotome blade 18 such that when the valvulotome blade 18 is in its proximally retracted position (FIGS. 2a, 5a) the entire cutting edge 26 of the blade 18 will be received within or will seat or nest within, the distal end of the catheter body 12, with the remaining portion of the valvulotome blade 18 protruding beyond the distal end of the catheter body 12. Thus, the distal end of the catheter body 12 and the blade 18 are correspondingly configured such that, when the blade 18 is in its proximally retracted position (FIGS. 2a & 5a) the blade 18 will be in smooth surface-to-surface abutment with the catheter body 12, thereby forming a blunt distal end on the device 10 to facilitate advancement of the device 10 through the vasculature without causing undue trauma or damage to the vascular surfaces.

The catheter body 12 includes an elongate pliable proximal tube 30 having a distal tube member 32 attached thereto. The lumen 34 of the catheter body 12 extends longitudinally through the proximal tube 30 and distal tube member 32, as shown. The distal tube member 32 has a lateral slot opening 36 and a blunt, beveled distal opening 38 formed therein, in communication with lumen 34. A retainer member 40 is disposed within the lumen 34 of the distal tube member 32 and is configured to engage the valvulotome blade 18 at its distal and proximal limits of travel, thereby serving to define the maximum distance of slidable back and forth movement that the blade 18 may undergo, and preventing inadvertent passage of the entire body of the blade 18 out of the distal end opening 38 of the lumen 30, as could result in undesired detachment of the blade 18 from the catheter body 12.

A control wire 42 extends longitudinally through the lumen 34 of the catheter body 12. The distal end of the control wire 42 is connected to the proximal end of the valvulotome blade 18. The proximal end of the control wire 42 extends into the handpiece 14 and is connected to the actuator 16. Movement of the actuator 16 in the forward direction (arrow A), causes the control wire 42 to slide in the distal direction within the lumen 34 of the catheter body 12.

Such distal slidable movement of the control wire 42 causes the valvulotome blade 18 to advance from its proximally retracted position (FIGS. 2a, 5a) to its distally advanced position (FIGS. 2b, 5b).

When the distal advancement of the valvulotome blade 18 reaches its distal limit, the valvulotome blade 18 will engage or abut against the retainer member 40. Such engagement or abutment of the valvulotome blade 18 against the retainer member 40 will prevent the valvulotome blade 18 from undergoing further distal movement in the distal direction. Thereafter, further distal advancement of the actuator 16 will cause a portion of the control wire 42 to protrude or bulge out of the lateral slot opening 36, as shown in FIG. 5b. The portion of the control wire 42 which bulges laterally out of the lateral slot opening 36 engages the adjacent wall of a blood vessel and causes the distal portion of the catheter body 12 to be forced against the opposite or contralateral wall of the blood vessel. This function of the bulging control wire 42 is described more fully herebelow in conjunction with the preferred method of using the present invention.

A proximal fluid infusion tube 50 is connected to the catheter body 12. The lumen of the fluid infusion tube 50 is in fluidic communication with the lumen 34 of the catheter body 12. A Leur connector 52 is mounted on the proximal end of the fluid infusion tube 50. Thus, fluid may be infused through fluid infusion tube 50, through the lumen 34 of the catheter body 12 and out of the lateral slot opening 36 and distal end opening 38. In some applications of the valvulotome device 10, it may be desirable to intermittently or continuously infuse clear fluids such as 0.9% NaCl solution or Ringer's lactate solution so as to displace any blood located within the lumen of the vein wherein the valvulotome device 10 is inserted, and to provide a visually transparent environment for angioscopic observation of the operation of the valvulotome device 10. This mode of operation of the device 10 is described more fully herebelow in connection with the preferred method of using the device 10.

B. The Preferred Method of Use

A preferred method of using the device shown in FIGS. 1–7 is illustrated, in step-by-step fashion, as shown in FIGS. 8a–8g.

FIGS. 8a–8g show a vein V, such as a saphenous vein, having a semilunar venous valve VV positioned therein.

In this example, an angioscope A is positioned within the lumen L of the vein V so as to visually observe the use of the device 10. This angioscope A may comprise any suitable type of angioscope capable of visualizing the use of the valvulotome device 10. In particular, the angioscope device A may be incorporated into, or combined with a side branch blocking device, such as that disclosed in copending United States Patent Application entitled SIDE BRANCH OCCLUSION CATHETER DEVICE HAVING INTEGRATED ENDOSCOPE FOR PERFORMING ENDOSCOPICALLY VISUALIZED OCCLUSION OF THE SIDE BRANCHES OF AN ANATOMICAL PASSAGEWAY, filed on even date herewith.

Also, during the steps of the method shown in FIGS. 8a–8f, blood will generally be displaced from the lumen L of the vein by infusing a clear liquid (e.g., 0.9% NaCl or Ringer's lactate solution) intermittently or continuously through the lumen 34 of device 10 and/or through one or more other cannulae inserted into the vein V, to provide a visually transparent environment for viewing of the operation of the valvulotome 10 by the angioscope A.

With reference to FIG. 8A, the valvulotome device 10 is initially configured with the actuator 15 in its proximally retracted position in contact with stop member 17. This will cause the valvulotome blade 18 to be disposed in its distally retracted position (see FIGS. 1a, 5a). Thereafter, insertion of the valvulotome device 10 into the lumen L of the vein V is accomplished by surgical cut-down of the vein V, or by percutaneous insertion of the device 10 using the Seldinger technique, or any other suitable insertion technique.

The angioscope A is positioned in retrograde fashion, as shown, and is utilized to visually verify when the distal end of the device 10 has become positioned immediately adjacent the upstream side of a venous valve VV, as shown in FIG. 8a. This may be expediently accomplished by initially advancing the distal end of the device 10 through the cusps of the venous valve VV, and thereafter, slowly retracting the device 10 in the proximal direction until the distal end of the device 10 has been drawn back through the venous valve VV and is positioned immediately upstream of the venous valve VV, as illustrated in FIG. 8a.

Thereafter, as shown in FIG. 8b, the actuator 16 is moved in the distal direction, thereby causing the control wire 42 and valvulotome blade 18 to advance in the distal direction, such that the distal portion of the valvulotome blade 18 extends through the venous valve VV. After the valvulotome blade 18 has reached its distal limit of travel, further advancement of the actuator 16 causes the control wire 42 to slacken and bulge out of the lateral slot opening 36 in a first direction, such that the bulging portion of the control wire 42 engages the luminal wall of the vein V. This propels the catheter body 12 in a direction opposite the first direction, thereby forcing the catheter body 12 against the contralateral luminal wall of the vein V, as shown in FIG. 8b. Such movement of the catheter body 12 against the contralateral wall of the vein V causes the smooth venous wall abutment surface 28 of the valvulotome blade 18 to also abut against the contralateral luminal wall of the vein V, immediately adjacent one cusp of the venous valve VV, as shown.

Thereafter, as shown in FIG. 8c, the device 10 is slowly pulled in the proximal direction such that the cutting edge 26 of the valvulotome blade 18 will cut through one cusp of the venous valve VV. This effectively renders incompetent one half of the venous valve VV.

Thereafter, as shown in FIG. 8d, the actuator 16 is returned to its fully proximally retracted position, thereby slidabley proximally retracting the control wire 42 into the lumen 34 of the catheter body 12, and causing the valvulotome blade 18 to retract to its distally retracted position. Thereafter, the device is rotated 180 degrees such that the valvulotome blade 18 becomes positioned for cutting of the remaining cusp of the venous valve VV.

Thereafter, as shown in FIG. 8e, the actuator 16 is again moved in the distal direction, such that the valvulotome blade 18 extends beyond the remaining cusp of the venous valve VV, and the control wire 42 again bulges out of the lateral slot opening 36 and engages the wall of the vein V, thereby forcing the catheter body 12 and venous wall abutment surface 28 of the blade 18 against the contralateral or opposite luminal wall of the vein V. In this regard, the device 10 is now in positioned for cutting of the remaining venous valve cusp VV, as shown in FIG. 8e.

Thereafter, the device 10 is again pulled in the proximal direction, such that the cutting edge 26 of the valvulotome blade 18, thereby resulting in incompetence of the entire venous valve VV. Thereafter, the actuator 16 is returned to its fully proximally retracted position, thereby causing the control wire 42 to become retracted into the lumen 34 of the catheter body 12 and the valvulotome blade 18 to resume its distally retracted position.

Thereafter, the angioscope A and valvulotome device 10 may be advanced further through the lumen L of the vein V and used to disrupt additional venous valves VV by the above-described method.

After all of the venous valves VV in the segment of vein V have been disrupted, the angioscope A and valvulotome device 10 are removed, and the lumen L of the segment of vein V is thereby rendered devoid of functional venous valves, as shown in FIG. 8g.

In some instances, the diameter of the vein V in which the device 10 is positioned will be so small that there will exist little or no space for protrusion of the control wire 42 out of the lateral slot opening 36. However, to insure consistency of operation and proper positioning of the valvulotome blade 18, it is desirable that the device be constructed such that the operator may consistently push the actuator 16 to its fully distally advanced position (arrow A), even when the vein V lacks sufficient size to permit complete or full bulging or protrusion of the guide wire 42 out of the lateral slot opening 36. To permit such full movement of the actuator 16 to its fully distally advanced position, even when there exists no space for protrusion of the control wire 42 out of the lateral slot opening 36, a coil spring member (not shown) is attached to the proximal side of the actuator 16 and is connected to the interior of the handpiece 14. The control wire 42 is connected to the actuator such that the control wire 42 will move in the distal direction along with distal movement of the actuator 16 to cause the valvulotome blade 18 to advance to its fully distally advanced position (FIGS. 2b & 5b), and also to further advance to cause the desired portion of the control wire 42 to slacken and bulge out of the lateral slot opening 36. However, in cases where there is not sufficient space for the control wire 42 to fully slacken and bulge out of the lateral slot opening 36, the actuator 16 may nonetheless be advanced to its full distal position, thereby sliding over its contacting portion of the control wire 42 and causing extension of the coil spring member (not shown) connected thereto. In this regard, the operator may effect full advancement of the actuator 16 to its full distal position even when there is insufficient space to permit full protrusion and bulging of the control wire 42 out of the lateral slot opening 36. However, when the operator releases the distally directed pressure on the actuator 16, the coil spring (not shown) will retract the actuator 16 to its original position relative to the control wire 42.

In summary, it will be appreciated that the invention has been described with reference to certain presently preferred embodiments of the invention. It will be recognized that various additions, deletions, alterations and modifications may be made to the above-described embodiments without departing from the intended spirit and scope of the invention. Accordingly, it is intended that all such additions, deletions, alterations and modifications be included within the scope of the following claims.

What is claimed is:

1. A valvulotome device for cutting venous valves within the lumen of a vein, said device comprising:
   an elongate shaft having a proximal end, a distal end, a longitudinal axis, and a lumen extending longitudinally therethrough;
   an elongate control member extending longitudinally through the lumen of said shaft;
   a valvulotome blade positioned on the distal end of said shaft and connected to the distal end of said control member, said valvulotome blade comprising an elongate shank portion which extends substantially parallel to the longitudinal axis of said shaft body, and a head portion which protrudes to one side of said shank portion, said head portion having a proximal cutting edge formed thereon;

said valvulotome blade and said control member being longitudinally moveable, back and forth, relative to said shaft, such that said blade is alternately positionable in:
  i. a proximally retracted position wherein the proximal cutting edge of said blade is shielded by the distal end of said shaft; and,
  ii. a distally extended position wherein the proximal cutting edge of said blade is located a spaced distance ahead of the distal end of said shaft such that retraction of said blade, in the proximal direction, through a venous valve will cause the proximal cutting edge of said blade to cut said venous valve;

wherein said proximally retracted position and distally extended position extend along the same longitudinal axis.

2. The device of claim 1 wherein said shaft comprises a rigid tubular cannula.

3. The device of claim 1 wherein said shaft comprises a pliable tubular catheter body.

4. The device of claim 1 further comprising:
a handpiece located at the proximal end of said shaft, said handpiece having a moveable actuator which is connected to the proximal end of said control member such that movement of said actuator in the proximal direction will cause said control wire and said valvulotome blade to move in the proximal direction, and movement of said actuator in the distal direction will cause said control wire and said valvulotome blade to move in the distal direction.

5. The device of claim 1 further comprising:
a fluid infusion inlet fluidly connected to said lumen of said shaft member such that fluid may be infused through the lumen of said shaft member.

6. The device of claim 5 wherein said fluid infusion inlet comprises:
a fluid infusion tube connected to the shaft member, said fluid infusion tube having a lumen formed therein in communication with said lumen of said shaft member, said fluid infusion tube being connectable to a fluid source to facilitate passage of fluid through the lumen of said shaft member.

7. The device of claim 1 wherein said valvulotome blade further comprises:
a venous wall abutment surface formed on the outer surface of the head portion of said valvulotome blade, said venous wall abutment surface being a spaced distance from said proximal cutting edge such that, when said venous wall abutment surface is placed in contact with the luminal wall of a vein, said proximal cutting surface will be maintained a distance of 0.020–0.025 inches away from said luminal wall of said vein.

8. The device of claim 7 wherein said venous wall abutment surface is of a smooth, generally convex configuration such that, said venous wall abutment surface may be placed in abutting contact with the luminal wall of the vein, and longitudinally moved while maintaining said abutting contact, without causing trauma to the luminal wall of said vein.

9. The device of claim 1 further comprising:

a lateral slot opening formed in said shaft near the distal end thereof, and forming a lateral passage out of the lumen in which said control member is positioned; and, a retainer member mounted in said shaft, said retainer member being configured and constructed to prevent said valvulotome blade from moving in the distal direction beyond a distal limit point;

said lateral slot opening and said retainer member thereby cooperating to cause a portion of said control member to bulge in a first direction out of said lateral slot aperture upon continued distal advancement of said control member after said valvulotome blade has reached its distal limit point.

10. The device of claim 1 wherein said elongate control member comprises a wire which extends longitudinally through the lumen of said shaft.

11. The device of claim 10 wherein said wire comprises:
a longitudinal wire core member; and,
an outer wire coil member tightly helically wound around the outer surface of said longitudinal wire core member.

12. A valvulotome device for cutting venous valves within the lumen of a vein, said device comprising:
an elongate shaft having a proximal end, a distal end, a longitudinal axis, and a lumen extending longitudinally therethrough;
a single elongate control member extending longitudinally through the lumen of said shaft;
a single valvulotome blade positioned on the distal end of said shaft and connected to the distal end of said control member, said valvulotome blade comprising an elongate shank portion which extends substantially parallel to the longitudinal axis of said shaft body, and a head portion which protrudes to one side of said shank portion, said head portion having a proximal cutting edge formed thereon;
said valvulotome blade and said control member being longitudinally moveable, back and forth, relative to said shaft, such that said blade is alternately positionable in:
  i. a proximally retracted position wherein the proximal cutting edge of said blade is shielded by the distal end of said shaft; and,
  ii. a distally extended position wherein the proximal cutting edge of said blade is located a spaced distance ahead of the distal end of said shaft such that retraction of said blade, in the proximal direction, through a venous valve will cause the proximal cutting edge of said blade to cut said venous valve.

13. The device of claim 12 wherein said shaft comprises a rigid tubular cannula.

14. The device of claim 12 wherein said shaft comprises a pliable tubular catheter body.

15. The device of claim 12 further comprising:
a handpiece located at the proximal end of said shaft, said handpiece having a moveable actuator which is connected to the proximal end of said control member such that movement of said actuator in the proximal direction will cause said control wire and said valvulotome blade to move in the proximal direction, and movement of said actuator in the distal direction will cause said control wire and said valvulotome blade to move in the distal direction.

16. The device of claim 12 further comprising:
a fluid infusion inlet fluidly connected to said lumen of said shaft member such that fluid may be infused through the lumen of said shaft member.

17. The device of claim 16 wherein said fluid infusion inlet comprises:

a fluid infusion tube connected to the shaft member, said fluid infusion tube having a lumen formed therein in communication with said lumen of said shaft member, said fluid infusion tube being connectable to a fluid source to facilitate passage of fluid through the lumen of said shaft member.

18. The device of claim 12 wherein said valvulotome blade further comprises:

a venous wall abutment surface formed on the outer surface of the head portion of said valvulotome blade, said venous wall abutment surface being a spaced distance from said proximal cutting edge such that, when said venous wall abutment surface is placed in contact with the luminal wall of a vein, said proximal cutting surface will be maintained a distance of 0.020–0.025 inches away from said luminal wall of said vein.

19. The device of claim 18 wherein said venous wall abutment surface is of a smooth, generally convex configuration such that, said venous wall abutment surface may be placed in abutting contact with the luminal wall of the vein, and longitudinally moved while maintaining said abutting contact, without causing trauma to the luminal wall of said vein.

20. The device of claim 12 further comprising:

a lateral slot opening formed in said shaft near the distal end thereof, and forming a lateral passage out of the lumen in which said control member is positioned; and, a retainer member mounted in said shaft, said retainer member being configured and constructed to prevent said valvulotome blade from moving in the distal direction beyond a distal limit point;

said lateral slot opening and said retainer member thereby cooperating to cause a portion of said control member to bulge in a first direction out of said lateral slot aperture upon continued distal advancement of said control member after said valvulotome blade has reached its distal limit point.

21. The device of claim 12 wherein said elongate control member comprises a wire which extends longitudinally through the lumen of said shaft.

22. The device of claim 21 wherein said wire comprises:

a longitudinal wire core member; and, an outer wire coil member tightly helically wound around the outer surface of said longitudinal wire core member.

23. A valvulotome device for cutting venous valves within the lumen of a vein, said device comprising:

an elongate shaft having a proximal end, a distal end, a longitudinal axis, and a lumen extending longitudinally therethrough;

an elongate control member extending longitudinally through the lumen of said shaft;

a valvulotome blade positioned on the distal end of said shaft and connected to the distal end of said control member, said valvulotome blade comprising:

an elongate shank portion which extends substantially parallel to the longitudinal axis of said shaft body and having an inner edge;

a head portion which protrudes to one side of said shank portion, said head portion having a proximal cutting edge formed thereon, said cutting edge having a concave configuration;

a venous wall abutment surface formed on the outer surface of the head portion of said valvulotome blade, with the cutting edge extending from the inner edge of the shank portion to a location which is a spaced distance from the outer-most extent of the venous wall abutment surface;

said valvulotome blade and said control member being longitudinally moveable, back and forth, relative to said shaft, such that said blade is alternately positionable in:

i. a proximally retracted position wherein the proximal cutting edge of said blade is shielded by the distal end of said shaft; and, ii. a distally extended position wherein the proximal cutting edge of said blade is located a spaced distance ahead of the distal end of said shaft such that retraction of said blade, in the proximal direction, through a venous valve will cause the proximal cutting edge of said blade to cut said venous valve.

24. The device of claim 23 wherein said shaft comprises a rigid tubular cannula.

25. The device of claim 23 wherein said shaft comprises a pliable tubular catheter body.

26. The device of claim 23 further comprising:

a handpiece located at the proximal end of said shaft, said handpiece having a moveable actuator which is connected to the proximal end of said control member such that movement of said actuator in the proximal direction will cause said control wire and said valvulotome blade to move in the proximal direction, and movement of said actuator in the distal direction will cause said control wire and said valvulotome blade to move in the distal direction.

27. The device of claim 23 further comprising:

a fluid infusion inlet fluidly connected to said lumen of said shaft member such that fluid may be infused through the lumen of said shaft member.

28. The device of claim 27 wherein said fluid infusion inlet comprises:

a fluid infusion tube connected to the shaft member, said fluid infusion tube having a lumen formed therein in communication with said lumen of said shaft member, said fluid infusion tube being connectable to a fluid source to facilitate passage of fluid through the lumen of said shaft member.

29. The device of claim 23 wherein said venous wall abutment surface is a spaced distance from said proximal cutting edge such that, when said venous wall abutment surface is placed in contact with the luminal wall of a vein, said proximal cutting surface will be maintained a distance of 0.020–0.025 inches away from said luminal wall of said vein.

30. The device of claim 29 wherein said venous wall abutment surface is of a smooth, generally convex configuration such that, said venous wall abutment surface may be placed in abutting contact with the luminal wall of the vein, and longitudinally moved while maintaining said abutting contact, without causing trauma to the luminal wall of said vein.

31. The device of claim 23 further comprising:

a lateral slot opening formed in said shaft near the distal end thereof, and forming a lateral passage out of the lumen in which said control member is positioned; and, a retainer member mounted in said shaft, said retainer member being configured and constructed to prevent said valvulotome blade from moving in the distal direction beyond a distal limit point;

said lateral slot opening and said retainer member thereby cooperating to cause a portion of said control member to bulge in a first direction out of said lateral slot aperture upon continued distal advancement of said control member after said valvulotome blade has reached its distal limit point.

32. The device of claim 23 wherein said elongate control member comprises a wire which extends longitudinally through the lumen of said shaft.

33. The device of claim 32 wherein said wire comprises:

a longitudinal wire core member; and, an outer wire coil member tightly helically wound around the outer surface of said longitudinal wire core member.

34. A method for cutting venous valves within the lumen of a vein, said method comprising the steps of:

a) providing a device comprising:

an elongate shaft having a proximal end, a distal end, a longitudinal axis, and a lumen extending longitudinally therethrough;

an elongate control member extending longitudinally through the lumen of said shaft;

a valvulotome blade positioned on the distal end of said shaft and connected to the distal end of said control member, said valvulotome blade comprising an elongate shank portion which extends substantially parallel to the longitudinal axis of said shaft body, and a head portion which protrudes to one side of said shank portion, said head portion having a proximal cutting edge formed thereon;

said valvulotome blade and said control member being longitudinally moveable, back and forth, relative to said shaft, such that said blade is alternately positionable in:

i. a proximally retracted position wherein the proximal cutting edge of said blade is shielded by the distal end of said shaft; and, ii. a distally extended position wherein the proximal cutting edge of said blade is located a spaced distance ahead of the distal end of said shaft such that retraction of said blade, in the proximal direction, through a venous valve will cause the proximal cutting edge of said blade to cut said venous valve;

b) causing said valvulotome blade of said device to be positioned in its proximally retracted position;

c) inserting the elongate shaft of said device, distal end first, into the vein wherein said venous valves are to be cut;

d) positioning said device such that the distal end of said shaft is slightly upstream of a first venous valve to be cut;

e) moving the valvulotome blade to its distally extended position, and causing the blade to be positioned such that the head portion of said valvulotome blade is located downstream of the venous valve;

f) moving the device in the proximal direction such that the proximal cutting edge of the valvulotome blade cuts a portion of said first venous valve;

g) returning the valvulotome blade of said device to its proximally retracted position;

h) rotating the device approximately 180°;

i) positioning the device such that the distal end of the elongate shaft is slightly upstream of said first venous valve;

j) moving the valvulotome blade of the device to its distally extended position such that the head portion of said valvulotome blade is positioned upstream of said venous valve;

k) moving the device in the proximal direction such that the proximal cutting edge of said valvulotome blade cuts said first venous valve, thereby rendering said venous valve fully incompetent; and l) concurrently positioning an angioscope within the vein and using the angioscope to visualize the positioning and use of said device during said cutting of said venous valves.

35. The method of claim 34 wherein said angioscope is incorporated into a side branch blocking device, said side branch blocking device being operative to effect in situ blocking of side branches which emanate from said vein, and wherein said method of claim 34 is performed in conjunction with the in situ blocking of said side branches, and wherein the angioscope incorporated into said side branch blocking device being used to visually observe both the side branch blocking procedure and the cutting of said venous valves.

36. The method of claim 34, further comprising the step of providing said device with:

a lateral slot opening formed in said shaft near the distal end thereof, and forming a lateral passage out of the lumen in which said control member is positioned; and, a retainer member mounted in said shaft, said retainer member being configured and constructed to prevent said valvulotome blade from moving in the distal direction beyond a distal limit point;

said lateral slot opening and said retainer member thereby cooperating to cause a portion of said control member to bulge in a first direction out of said lateral slot aperture upon continued distal advancement of said control member after said valvulotome blade has reached its distal limit point.

37. The method of claim 36, wherein the performance of steps E and F of said method further comprise causing a portion of said control member to protrude out of said lateral slot opening and into contact with the luminal wall of the vein so as to force the venous wall abutment surface of the head portion of the valvulotome blade into contact with the luminal surface of the vein during the performance during steps E and F of said method, and wherein the performance of step G of said method further comprises causing said control member to be retracted into said lateral slot opening and into the shaft of said device, thereby terminating the forcing of said venous wall abutment surface of the said head portion of the valvulotome blade against the luminal surface of the vein.

* * * * *